United States Patent
McVey et al.

(10) Patent No.: US 6,558,529 B1
(45) Date of Patent: May 6, 2003

(54) ELECTROCHEMICAL SENSOR FOR THE SPECIFIC DETECTION OF PEROXYACETIC ACID IN AQUEOUS SOLUTIONS USING PULSE AMPEROMETRIC METHODS

(75) Inventors: Iain F. McVey, Lakewood, OH (US); Brian J. DeSantis, Chicago, IL (US); Jan J. Lewandowski, South Euclid, OH (US); Karen L. Thomas, Eastlake, OH (US); Brian E. Schindly, Mentor, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/499,421

(22) Filed: Feb. 7, 2000

(51) Int. Cl.$^7$ ............................................... G01N 27/26
(52) U.S. Cl. ............................ 205/787; 134/2; 134/42; 134/113; 134/201; 204/400; 204/402; 204/412; 205/775
(58) Field of Search ................................. 205/775, 787; 204/400, 402, 412

(56) References Cited

U.S. PATENT DOCUMENTS

| | | | |
|---|---|---|---|
| 2,846,386 A | * | 8/1958 | Ingruber |
| 3,196,100 A | * | 7/1965 | Digby |
| 3,644,824 A | | 2/1972 | Barker et al. |
| 4,216,069 A | | 8/1980 | Olson |
| 4,505,784 A | * | 3/1985 | Mund et al. |
| 4,566,949 A | * | 1/1986 | Berger |
| 4,571,292 A | | 2/1986 | Liu et al. |
| D292,229 S | | 10/1987 | Knudson et al. |
| 4,857,152 A | | 8/1989 | Armstrong et al. ............. 204/1 |
| 4,897,162 A | | 1/1990 | Lewandowski et al. |
| 4,947,153 A | | 8/1990 | Berger |
| 5,131,999 A | | 7/1992 | Gunasingham |
| 5,214,964 A | | 6/1993 | Hartfiel |
| 5,310,524 A | | 5/1994 | Campbell et al. |
| 5,364,510 A | | 11/1994 | Carpio |
| 5,366,609 A | | 11/1994 | White et al. |
| 5,374,892 A | | 12/1994 | Sturrock et al. |
| 5,395,493 A | | 3/1995 | Pinkowski ............... 204/153.1 |
| 5,400,818 A | | 3/1995 | Cosentino et al. |
| 5,470,484 A | | 11/1995 | McNeel |
| 5,494,637 A | | 2/1996 | Barlow |
| 5,503,720 A | | 4/1996 | Teske .......................... 205/787 |
| 5,644,501 A | | 7/1997 | Lin et al. |
| 5,873,990 A | | 2/1999 | Wojciechowski et al. ... 204/406 |
| 6,203,767 B1 | | 3/2001 | Leasko ........................ 422/292 |

FOREIGN PATENT DOCUMENTS

| | | |
|---|---|---|
| DE | 44 12 576 | 10/1995 |
| EP | 0 833 149 | 4/1988 |
| EP | 0 269 435 | 6/1988 |
| EP | 0333246 A2 | 3/1989 |

OTHER PUBLICATIONS

Analytical Chemistry, vol. 62, No. 10, May 15, 1990 (pp. 589A–597A).

* cited by examiner

Primary Examiner—T. Tung
(74) Attorney, Agent, or Firm—Fay, Sharpe, Fagan, Minnich & McKee, LLP (57) ABSTRACT

An electrochemical sensor (A, A') is specific for the detection of peroxyacetic acid in a solution which also contains hydrogen peroxide. A potential is applied between a reference electrode (120, 120') and a working electrode (118, 118'). A read voltage (FIG. 7) is selectively pulsed across a counter electrode (122, 122') and the working electrode. The current flowing between the working electrode and the counter electrode is dependent on the peroxyacetic acid concentration in the solution (FIG. 6). By careful selection of the read voltage, the contribution of hydrogen peroxide to the current flow is virtually negligible. The sensor effectively measures peroxyacetic acid concentrations in the range generally employed in sterilization and disinfection baths (100–3000 ppm.).

25 Claims, 6 Drawing Sheets

ELECTROCHEMICAL SENSOR FOR THE SPECIFIC DETECTION OF PEROXYACETIC ACID IN AQUEOUS SOLUTIONS USING PULSE AMPEROMETRIC METHODS

BACKGROUND OF THE INVENTION

The present invention relates to the sterilization and disinfection arts. It finds particular application in conjunction with the detection of peroxyacetic acid concentrations in solutions used for sterilization or disinfection of medical, dental, and pharmaceutical equipment and will be described with particular reference thereto. It should be appreciated, however, that the invention is also applicable to detection of peroxyacetic acid and other oxidizable chemicals in solution, such as hydrogen peroxide.

Peroxyacetic acid, or peracetic acid, is a useful sterilant and/or disinfectant for a variety of applications, including disinfection of waste and sterilization or disinfection of medical, dental, pharmaceutical, or mortuary equipment, packaging containers, food processing equipment, and the like. It has a broad spectrum of activity against microorganisms, and is effective even at low temperatures. It poses few disposal problems because it decomposes to compounds which are readily degraded in sewage treatment plants. Peroxyacetic acid solutions also have the ability to be reused over a period of time, allowing instruments to be sterilized or disinfected throughout the day in the same bath of sterilant.

In use, peroxyacetic acid precursors are typically mixed with water and other chemicals in order to create a sterilant solution. Items to be sterilized or disinfected are then immersed in the sterilant. Decontaminated items are then rinsed to remove traces of the acid and other cleaning chemicals, before use. To ensure effective sterilization or disinfection within a preselected period of time, the concentration of peroxyacetic acid is maintained above a selected minimum effective level. Disinfection is typically carried out at lower concentrations of peroxyacetic acid than for sterilization. When the peroxyacetic acid concentration is at or above the minimum effective level, complete sterilization or disinfection is expected.

Because the peroxyacetic acid tends to decompose over time, it is valuable to monitor the sterilant periodically to determine the level of peroxyacetic acid. The level can be compared against preselected minimum levels, used to adjust contact time, used to control concentration, or the like. Currently, it is often assumed that the sterilant will remain at or above the minimum effective concentration. However, differences in the temperature of the sterilant, the quantity of items sterilized or disinfected, and the degree and nature of contamination of the items all result in considerable variations in the degradation of the sterilant. In addition, storage conditions and duration sometimes lead to degradation of the peroxyacetic acid precursors before use.

Methods currently used to detect peroxyacetic acid are often unable to distinguish between peroxyacetic acid and other compounds typically present in the solution, such as hydrogen peroxide and acetic acid. Dippable papers are easy to use, but lack accuracy, particularly at concentrations suitable for sterilization or disinfection. Chemical titration methods provide a more accurate measure of the peroxyacetic acid in solution, but are time consuming to perform and are not readily automated. Frequently, more than one titration is performed to eliminate the contribution of hydrogen peroxide to the result.

Recently, a number of electrochemical techniques have been developed for detection of oxidizable or reducible chemical species, such as peroxyacetic acid. Consentino, et al., U.S. Pat. No. 5,400,818, discloses a sensor for peroxyacetic acid-hydrogen peroxide solutions. The sensor measures the resistivity of the solution, which is dependent on both the peroxyacetic acid and the hydrogen peroxide concentrations, as well as other factors. Thus, the sensor is unable to differentiate between the two components.

European Patent Application EP 0 333 246 A, to Unilever PLC, discloses an electrochemical sensor for detection of oxidizable or reducible chemical species using an amperometric method in which a fixed potential is maintained between a reference and a working electrode. The current at the working electrode is used to determine the concentration of peroxyacetic acid. Other species present, however, influence the current flowing, and hence the accuracy of the results.

Teske, U.S. Pat. No. 5,503,720, discloses a process for the determination of reducible or oxidizable substances, such as peroxyacetic acid in sewage waste. The process uses potentiostatic amperometry to detect peroxyacetic acid concentrations. The technique, however, depends on the achievement of a steady state, which frequently takes several hours.

Conventional electrochemical detection systems often employ a porous membrane, which separates the sample to be analyzed from the electrodes. Charged species pass through the membrane when traveling to the electrodes. This increases the time for measurements to be made and adds complexity and cost to the system.

The present invention provides a new and improved sensor and method for the selective detection of peroxyacetic acid which overcomes the above referenced problems and others.

SUMMARY OF THE INVENTION

In accordance with one aspect of the present invention, a decontamination process is provided. The process includes circulating a decontaminant solution including peroxyacetic acid though a treatment vessel which contains items to be decontaminated. The process further includes withdrawing a sample of the decontaminant solution into a chamber to contact a working electrode and a counter electrode and pulsing a voltage between the working electrode and the counter electrode at a selected voltage relative to a reference electrode and measuring the output current generated. The voltage is selected such that the current generated is substantially dependent on a concentration of the peroxyacetic acid in the sample and substantially independent of a concentration of another oxidizing species in the sample.

In accordance with another aspect of the present invention, a method of detecting a first oxidizing species in a solution to be tested is provided. The solution also contains a second oxidizing species. The method includes disposing a working electrode and a counter electrode in the solution, pulsing a read voltage in the diffusion limiting range across the working electrode and the counter electrode, and detecting current flowing between the working electrode and the counter electrode. The read voltage is selected such that the current flowing is substantially dependent on the concentration of the first oxidizing species and substantially independent of the concentration of the second oxidizing species in the solution.

In accordance with another aspect of the present invention, a decontamination apparatus is provided. The apparatus includes a decontamination vessel which receives items to be decontaminated. A fluid flow path circulates a decontaminant ion solution through the vessel. A sensor system is fluidly connected with the fluid flow path for specifically detecting the decontaminant in the decontaminant solution. The system includes a chamber which receives a sample of the decontaminant solution from the fluid flow path, a working electrode, and a counter electrode disposed within the chamber to contact the sample of decontaminant solution. An amperometric controller is electrically connected with the working and counter electrodes. The controller selectively pulses a preselected read voltage between the working electrode and the counter electrode and detects an output current flowing in a circuit including the working electrode, the counter electrode, and the solution. The read voltage is selected such that the output current is substantially dependent on the decontaminant concentration and substantially independent of the concentration of another oxidizing species in the solution.

One advantage of the present invention is that it enables the peroxyacetic acid concentration of a sterilizing or disinfecting solution to be determined rapidly, (i.e., in less than one minute) and without interference by other oxidizing species present in the solution.

Another advantage of the present invention is that the sensor confirms that a minimum effective concentration of peroxyacetic acid is maintained for effective sterilization or disinfection.

Yet another advantage of the present invention is the provision of a disposable sensor probe that requires no calibration before use.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
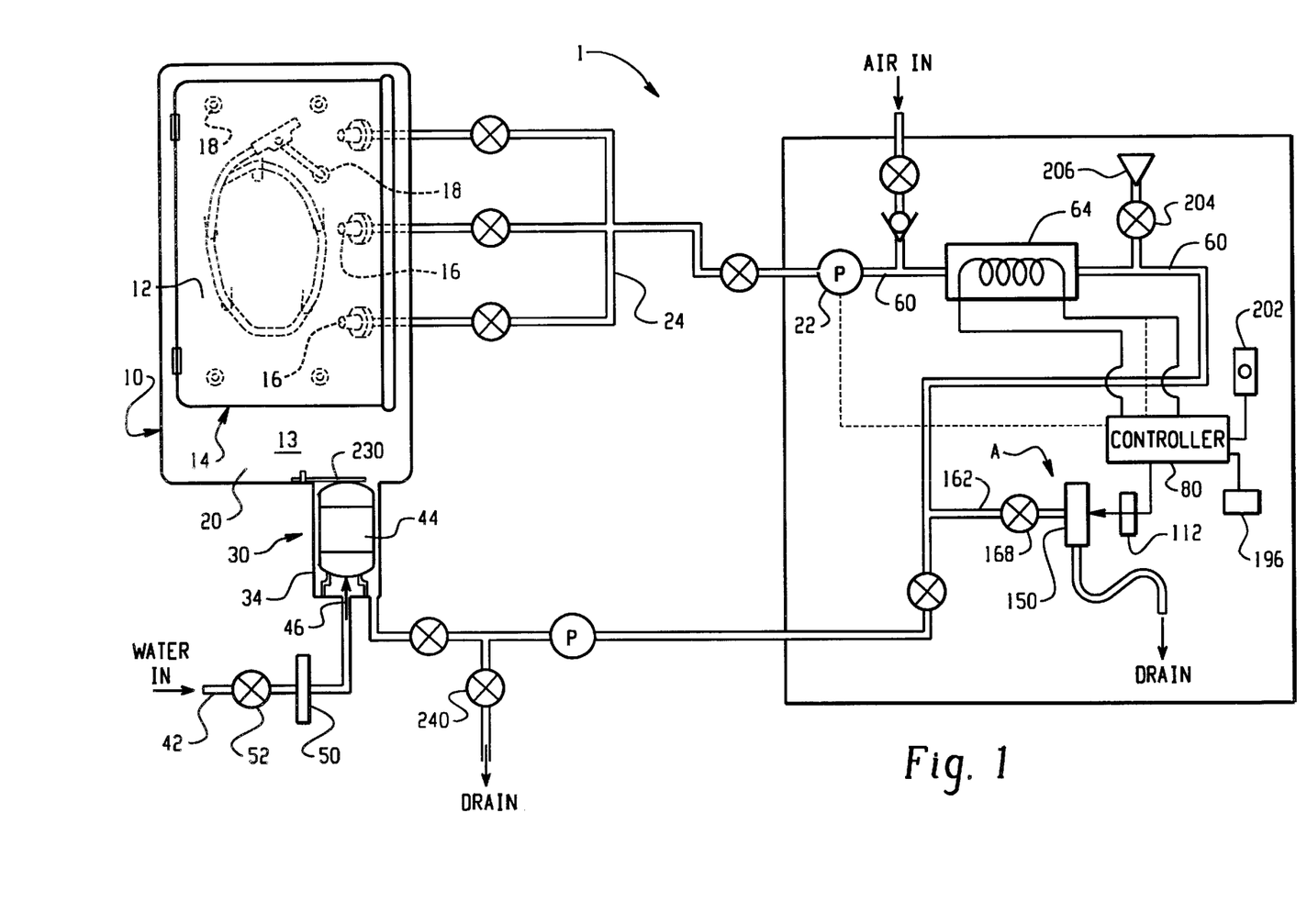
FIG. 1 is a plumbing diagram of a peroxyacetic acid sterilization and disinfection system according to the present invention.

With reference to FIG. 1, a peroxyacetic acid monitoring system or sensor A measures peroxyacetic acid concentrations in the presence of hydrogen peroxide. The monitoring system will be described with reference to an automated liquid decontamination apparatus 1 which sequentially cleans items, such as endoscopes or other medical, dental, and pharmaceutical devices, and the like, and then sanitizes, sterilizes, or disinfects them with a decontaminant solution which contains peroxyacetic acid. It should be appreciated, however that the monitoring system is also applicable to the measurement of peroxyacetic acid concentrations in other treatment systems and peroxyacetic acid-containing liquids.

The term "decontamination" and other terms relating to decontaminating will be used herein to describe sanitizing, sterilization, disinfection, and other antimicrobial treatments which are designed to destroy microorganisms contaminating the items.

The system 1 includes a decontamination cabinet 10 which defines an interior decontamination chamber 12. Items to be sterilized, disinfected, sanitized, or otherwise microbially decontaminated are loaded into the decontamination chamber through an opening in a front wall 13 of the cabinet, illustrated as closed by a door 14. Within the chamber, several spray jets or nozzles 16 spray a decontaminant solution over the items. Optionally, in the case of instruments with lumens, or other internal passages, some of the nozzles act as fluid ports 18 which are configured for interconnection with internal passages of the endoscopes and other objects with lumens, for supplying decontaminant solution and other liquids to the internal passages.

A collection tank or sump 20 forms the base of the cabinet 10 and receives the sprayed decontaminant solution as it drips off the items. A high pressure pump 22 delivers the decontaminant solution under pressure to the nozzles 16 and fluid ports 18 through a fluid distribution system or manifold 24.

A source 30 of a decontaminant solution preferably includes a well or mixing chamber 34. The well receives a dose of a concentrated decontaminant, such as an antimicrobial agent or reagents which react to form an antimicrobial agent on mixing with water. As shown in FIG. 1, the well is preferably integral with the collection tank 20 of the chamber, although a separate well is also contemplated.

A preferred antimicrobial agent is peroxyacetic acid, either in concentrated liquid form, or as a reaction product of powdered reagents, such as acetyl salicylic acid and sodium perborate. A water inlet 42 supplies water, typically from a municipal water system to the well. The water mixes with detergents, corrosion inhibitors, the concentrated decontaminant, and other selected components in the well to form wash, decontaminant, or other solutions.

Preferably, the concentrated decontaminant and the other components are supplied in a disposable package or cup 44 which is positioned in the well 34 prior to a decontamination cycle. The cup 44 holds a measured dose of the concentrated decontaminant. Optionally, a cleaner concentrate is also contained in the cup for forming a cleaning solution to clean the items prior to antimicrobial decontamination. The cup 44 may include a number of compartments which separately contain the cleaning concentrate and decontaminant concentrate for separate release into the system. In this way, the items are first cleaned and then microbially decontaminated.

In a preferred embodiment, the cup holds a cleaning concentrate in a first compartment. A second compartment holds pretreatment components, such as buffers for adjusting the pH, surfactants, chelating agents, and corrosion inhibitors for protecting the components of the system and items to be decontaminated from corrosion by the decontaminant.

A decontaminant, such as concentrated liquid peroxyacetic acid solution (or reagents that react to form it) is held in a third compartment. A cup cutter 46, or other suitable opening member, is positioned at the base of the well 34 for opening selected compartments of the cup, in sequence.

Alternatively, a solid or liquid concentrated decontaminant is supplied to the system from a separate bulk source (not shown), or is supplied to the system as the decontaminant solution, in an already-diluted form.

The water used for diluting the cleaner concentrate and decontaminant may be tap water or treated water, such as distilled water, filtered water, microbe free water, or the like. The quantity of water entering the system is regulated to provide a decontaminant solution of a desired concentration in the decontamination chamber 12. The water is preferably passed through a microporous filter 50 in the water inlet line 42 which filters out particles of dirt and microorganisms. A valve 52 in the water inlet 42 closes when the selected quantity of water has been admitted.

A fluid supply pathway 60 connects the well 34, the pump 22, and the fluid distribution system 24. A heater 64, situated in the fluid supply pathway 60, heats the decontaminant solution and optionally the cleaning solution and rinse liquid to a preferred temperature(s) for effective cleaning, decontamination, and rinsing. A temperature of about 50–60° C. is preferred for sterilization with peroxyacetic acid. The pathway 60 returns the sprayed decontaminant solution from the sump 20 to the manifold 24, and thence to the nozzles 16 and the fluid ports 18 via a recirculation valve. At least a portion of the sprayed decontaminant solution is directed through the well 34 before being returned to the decontamination chamber. This ensures thorough mixing of the concentrated decontaminant and other components with the solution before returning the decontaminant solution to the nozzles 16, 18.

The peroxyacetic acid monitoring system A detects the concentration of peroxyacetic acid passing through the fluid lines. FIG. 1 shows the system connected with the line 60. It should be appreciated, however, that the sensor is also conveniently connected with or disposed in any of the fluid flow lines of the system. A computer control system 80 controls the operation of the peroxyacetic acid monitoring system A. Preferably, the control system also controls the operation of other elements of the system 1, including the introduction of the cleaner concentrate, the peroxy concentrate, and other reagents as well as the pump 22, the heater 64, the valves 52, 68 and the like. The control system 80 may control one or more additional systems 1, if desired.

Figure 2:
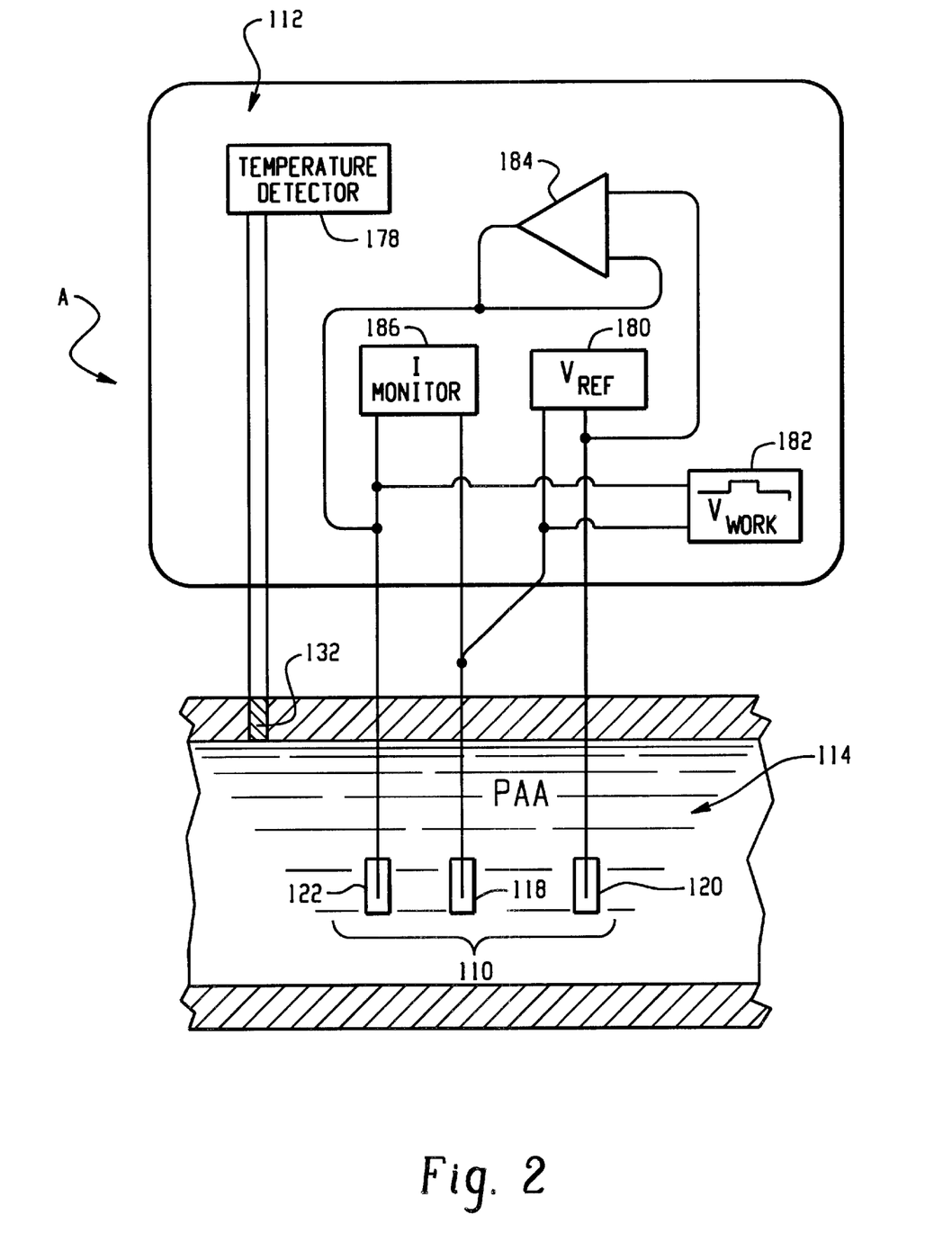
FIG. 2 is a schematic diagram of an electrochemical system for detecting peroxyacetic acid using pulse amperometry according to the present invention.

With reference now to FIG. 2, the system A for selective detection of peroxyacetic acid includes an electrode system 110, and an amperometric controller 112. The controller 112 both applies voltages and detects current flows in the system A. Although the controller is shown as a single unit in FIG. 2, it should be understood that a combination of pieces of electrochemical equipment generally known in the art which serves these functions is also contemplated.

The electrode system 110 is disposed in a reservoir 114 which receives a peroxyacetic acid solution to be tested, or may be placed directly in the recirculation path of the automated processor 1. Preferably, as shown in FIG. 1, the reservoir comprises a separate chamber, into which a sample of the circulating decontaminant solution is withdrawn at intervals. Because peroxyacetic acid is generally in equilibrium with hydrogen peroxide when in solution, the solution to be tested invariably contains some hydrogen peroxide.

The electrode system 110 includes three electrodes, namely a working electrode 118, a reference electrode 120, and a counter electrode 122. The reference electrode produces a constant electrical potential (or base potential). A suitable reference electrode 120 is a silver/silver chloride electrode. The working electrode is preferably an electroactive substance for peroxyacetic acid, such as carbon, gold (either alone, or doped with an inert material), or platinum. A particularly preferred working electrode 118 is amorphous, glassy carbon. Carbon is an effective electroactive substance for peroxyacetic acid and is highly selective for peroxyacetic acid in the presence of hydrogen peroxide. Carbon electrodes are also relatively resistant to peracetic acid, giving them a longer useful life. Glassy carbon is a particularly effective working electrode for measurements in the diffusion limited region. The counter electrode 122 is preferably formed from an inert conductive material, such as carbon, which readily accepts electrons. Alternatively, suitable counter electrodes are formed from silver, gold, or titanium.

Figure 3:
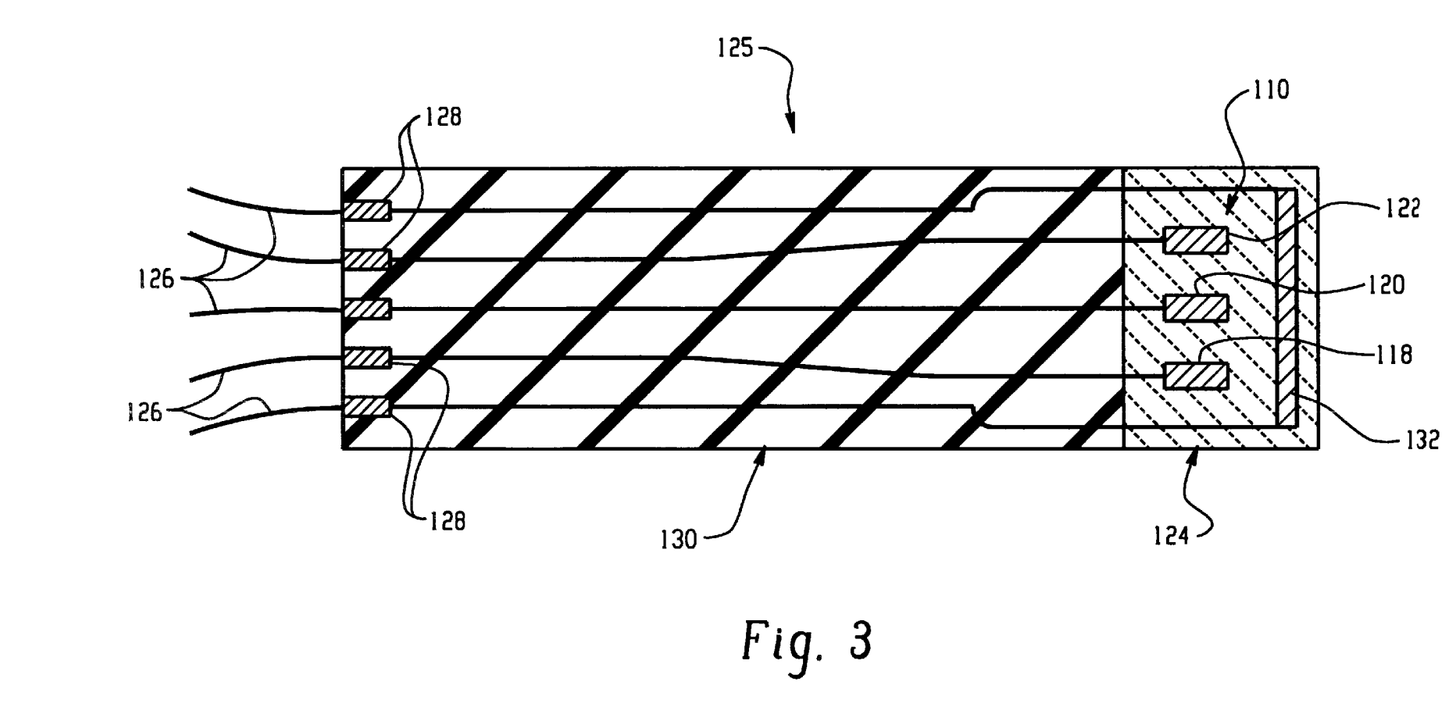
FIG. 3 is a top view of a disposable sensor for detecting peroxyacetic acid according to one embodiment of the present invention.

With reference to FIG. 3, in one embodiment, a substrate 124, preferably formed from an inert polymeric or ceramic sheet, supports the electrode system 110 to form a disposable probe 125. Electric leads 126 electrically connect the electrodes and the controller 112 through connecting points 128. Optionally, the sensor probe also includes an insulation layer 130 which covers the substrate and the leads around the connection points. The insulation layer inhibits the leads from participating in the electrochemical reactions. Optionally, a thermistor 132 detects the temperature of the sample in the region around the probe.

The sensor probe 125 is preferably constructed by thin film printing technology, although other methods of probe formation are also contemplated. In one embodiment, components of the sensor, including electrodes, electrical connection points and electrical leads are all laid down on the substrate. Materials for the electrodes and connection points are separately dispersed in inks and printed onto the substrate. The inks are cured, for example, by heat, UV light, or the like. The probes produced are inexpensive and thus are suited to single use. Additionally, such probes can be used without prior calibration. The electrode materials are selected so that they will not become disbanded when immersed in a peroxyacetic acid solution at temperatures between around 25° C. and 75° C. The choice of ink also affects the conductivity to some degree.

Figure 4:
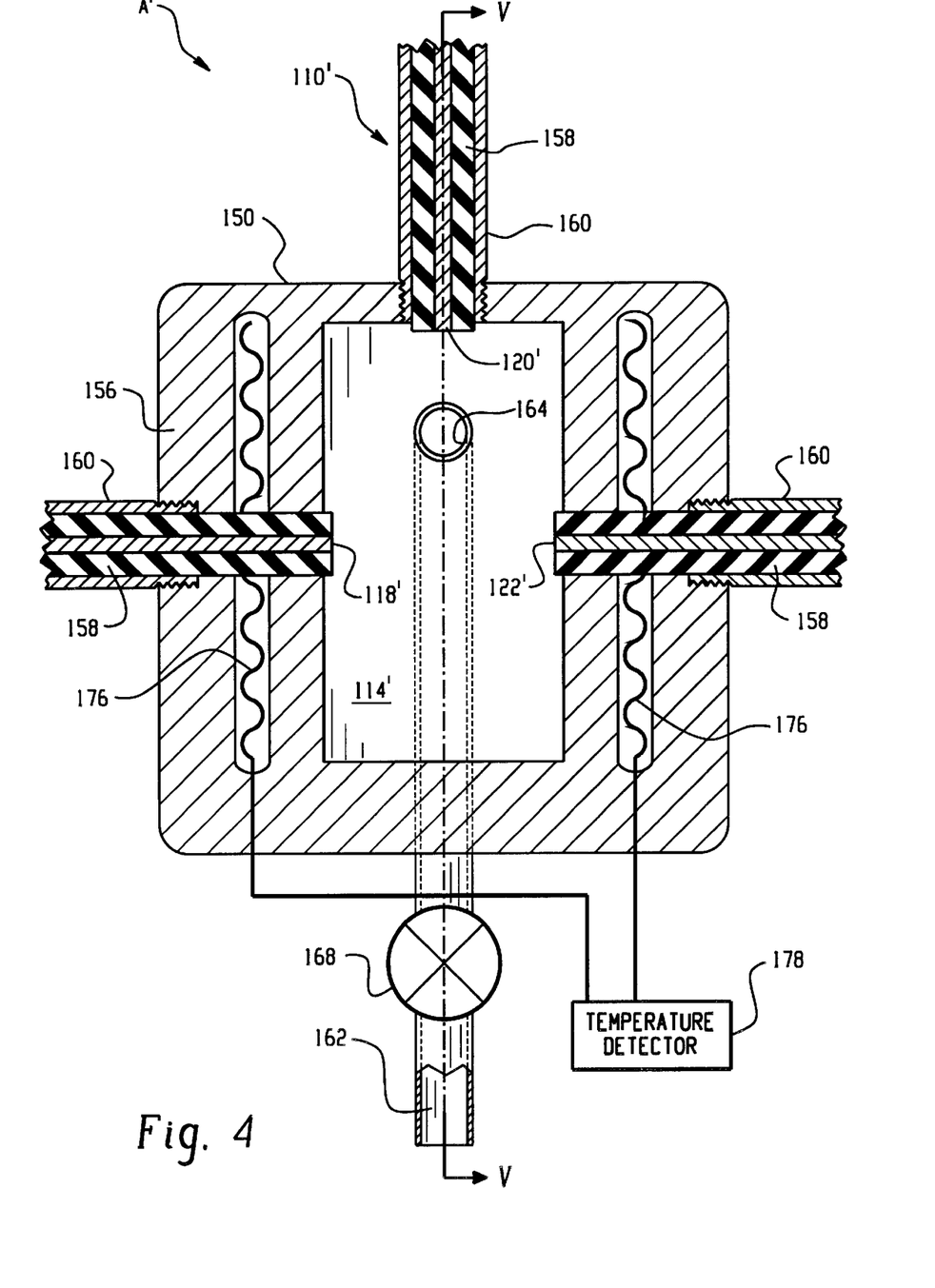
FIG. 4 is a side view of a reusable sensor system, according to another embodiment of the present invention.
Figure 5:
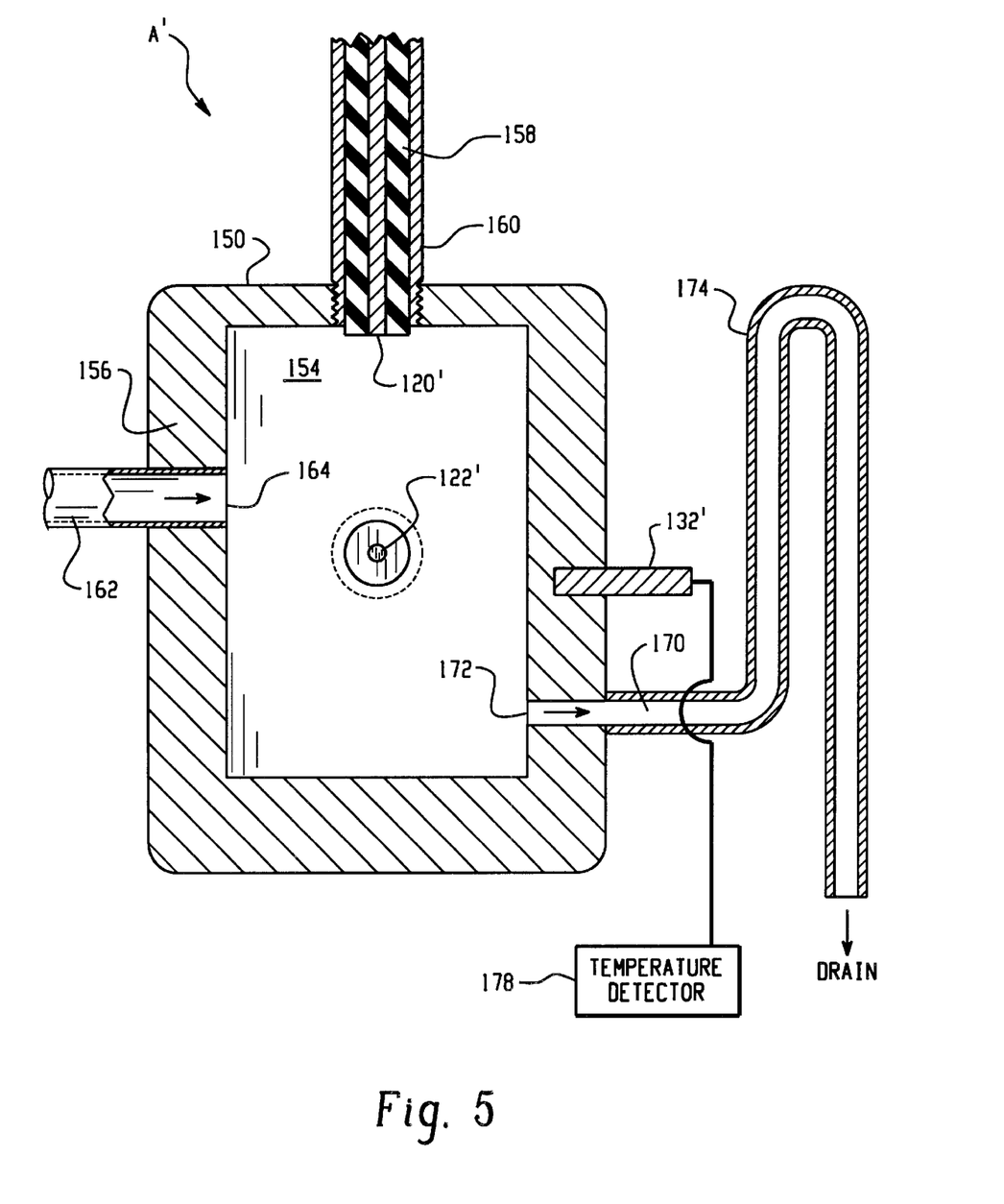
FIG. 5 is a side view through section V—V of the reusable sensor system of FIG. 4.

In another embodiment, shown in FIGS. 4 and 5, where like components are numbered with a prime ('), a sensor A' includes a durable, reusable electrode system 110' is shown. The electrode system 110' comprises a working electrode 118', a reference electrode 120' and a counter electrode 122'. The electrodes are analogous to those described above for the disposable sensor, but in this embodiment, are constructed to be reusable. The electrodes are mounted in a housing 150 formed from stainless steel or other material with a large heat capacity.

The housing 150 defines an interior chamber or reservoir 114'. Working faces of the three electrodes 118', 120', 122' project through walls 156 of the housing into the chamber. The electrodes are sheathed with and receive mechanical support from insulating material 158 so that only the working faces are exposed to the peroxyacetic acid sample. Steel tubes 160 are threadably, or otherwise removably attached to the walls of the chamber and carry the electrodes therethrough for ease of insertion and removal of the electrodes from the chamber and for mechanical support exterior to the chamber.

An inlet line 162 carries a sample of the circulating decontaminant solution into the chamber through an inlet 164 formed in one wall of the housing 150. A diaphragm valve 168 in the inlet line is normally closed, except when a sample is being taken. An overflow or drain line 170 carries fluid from the chamber via an outlet 172 defined through an opposite wall of the chamber. The overflow line leads to a drain via an inverted U-bend or trap 174 or returns the sample to the fluid flow line 60. It is preferred to direct the decontaminant solution to drain since this eliminates the need to assure sterility of reservoir surfaces of the sensor housing.

The chamber 114' and housing 150 are configured such that the thermal mass of the housing is substantially greater than the volume of the decontaminant solution to be sampled. The internal volume of the chamber is preferably about 10–15 ml or less. One or more thermal elements 176, within the walls 156 of the housing, maintains the housing at a stable temperature, and thereby the sampled fluid. Preferably, the sample is heated to a measurement temperature only slightly above the maximum temperature expected in the circulating fluid. This allows the sample to reach the measurement temperature very quickly. For example, if the decontamination portion of the cycle operates at about 50–55° C., the walls are preferably maintained at about 60° C. Alternatively, the sample may be cooled by cooling elements, such as by Peltier elements, to achieve an optimum measuring temperature. A thermocouple 132', or other temperature detector, detects the temperature of the chamber walls or the sampled fluid in the chamber. A temperature detector 178 receives signals from the thermocouple and adjusts the thermal elements to maintain the walls at a constant temperature. Alternately, compensation for temperature fluctuations can be made in the calculation of concentration, the currents from the electrodes, or the like. Preferably, the large, heated mass of the housing quickly brings the sample to a reproducible as well as stable temperature.

When a sample is to be taken, the valve 168 opens and allows the sampled fluid to flow into the chamber. The valve 168 remains open for sufficient time to allow the sampled fluid to flush the contents of the chamber through the overflow and replace the contents with freshly sampled fluid. In the system 1, the pump 22 pressurizes the circulating decontaminant to about 70 psi. In this case, a flush and fill period of around three seconds is sufficient to fill the chamber with a fresh sample of decontaminant solution. The valve is then closed and the sample is held within the chamber for sufficient time to equilibrate the temperature and for the sampled fluid to become quiescent. Once this equilibration period is complete, a pulsed voltage sequence is applied to the electrodes, resulting in the generation of an electrical current which is correlated to the concentration of peroxyacetic acid in the sample. The sampling and measurement steps are repeated, preferably every one to two minutes, to ensure that the peroxyacetic acid concentration does not drop below a minimum acceptable level.

With reference once more to FIG. 2, the amperometric controller 112 includes a voltage regulator 180 which applies a reference voltage (relative to the potential generated by the reference electrode) between the reference electrode 120 and the working electrode 118 of the embodiment of either FIG. 3 or FIGS. 4 and 5. A voltage pulser 182 superimposes a read voltage between the working and counter electrodes in short pulses.

Since reference electrodes do not tend to conduct electricity well, this may lead to resistance problems. It is desirable for the counter electrode 122 to be held at a potential sufficient to prevent current from flowing through the reference elecrode. This is readily achieved by using operational amplifiers 184, connected between the reference electrode 120 and counter electrode 122, which hold the reference electrode and the counter electrode at the same electrical potential. The amplifiers only allow current to flow through the sampled solution between the working and the counter electrode. This allows precise control of the applied potential while blocking the reference electrode against carrying electrical current. The reference potential of the reference electrode is thus used to calibrate/control the voltage potential applied between the working and counter electrodes so that the signal generated is well controlled.

The controller 112 also includes a current monitor 186 which detects the current flowing between the working and counter electrodes.

At a given temperature, the current measured is dependent on both the peroxyacetic acid concentration and the concentration of other oxidizing species, such as hydrogen peroxide, in the solution tested. The respective contributions of each of these components to the overall current measured is dependent on the selected read voltage. Over a limited read voltage range, which is partially dependent on the temperature of the solution, the hydrogen peroxide (or other oxidizing species present) has a much smaller influence on the current than the peroxyacetic acid. Thus, by carefully selecting a read voltage which minimizes the effect of other oxidizing species, the current measured is virtually independent of the concentration of hydrogen peroxide and shows a linear relationship with peroxyacetic acid concentration. For solutions containing peroxyacetic acid and hydrogen peroxide, the read voltage is preferably in the range of −1.2 volts to −1.6 volts, more preferably about −1.4 volts, relative to an Ag/AgCl reference electrode, when the working electrode and counter electrode are both carbon. When the working and counter electrode is gold, a preferred read voltage is about −50 mV. Obviously, if a different reference electrode and corresponding different base potential are employed, the read voltage relative to the reference electrode will change accordingly.

Figure 6:
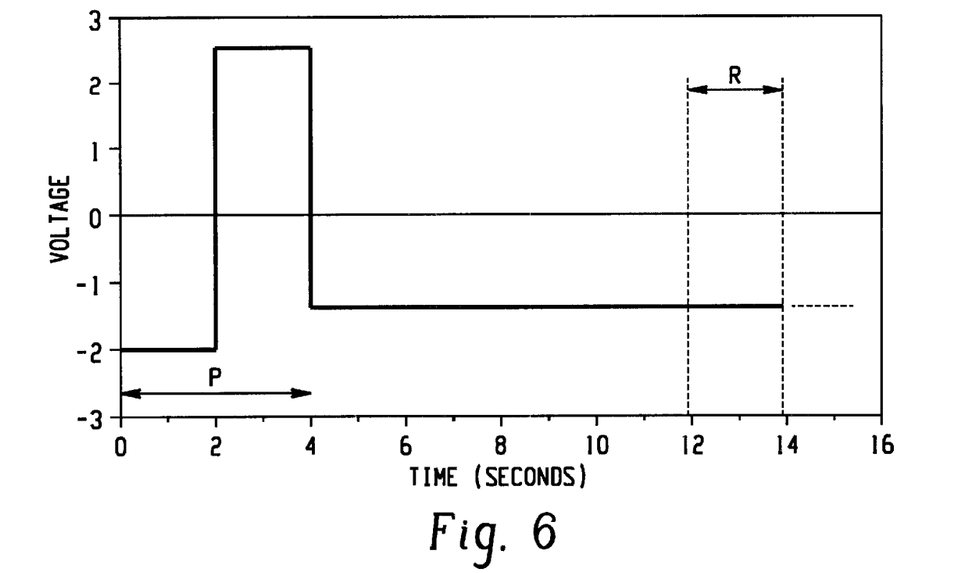
FIG. 6 is a plot showing a pulse sequence applied between working and counter electrodes of the sensor system of FIG. 1.

With reference now to FIG. 6, a typical measurement sequence includes a preconditioning phase P and a read phase R. The preconditioning phase enhances the quality of the current signal received in the read phase. A preferred preconditioning phase P includes applying a conditioning voltage pulse between the working electrode 118 and counter electrode 122 at about −2 volts for about 2 seconds, followed by about +2.5 volts for about 2 seconds. A sensing pulse at the read voltage (about −1.4 volts) is then applied for about 10 seconds.

The current flowing during the read pulse decays asymptotically to a steady value. Preferably, the current is measured towards the end of the application of the read voltage when its value has substantially reached steady state. For example, the current flowing during the last two to three seconds of the sensing pulse (the read phase) is measured and averaged to produce the signal that is used to measure the concentration of peroxyacetic acid. This allows time for the decay of any double layer formed on the measurement electrode and the establishment of a diffusion-limited current so that the current measured is derived from primarily faradaic reactions, rather than the primarily capacitive currents which occur in the double layer.

The pulse sequence of FIG. 6 is repeated a plurality of times during the antimicrobial stage of the cycle, each time with a new sample of the circulated solution. Any residue build-up at the end of cycle is electrochemically removed at the beginning of the next cycle. More specifically, after the last measurement, liquid is retained in the electrolytic cell either by retaining the last sample or by filling the cell with rinse water in the subsequent rinse stage.

In the next cycle, the cell samples the solution after the buffers, wetting agents, and corrosion inhibitors have been circulated, but before the antimicrobial is added. With the sampled buffer solution, voltage pulses are applied between the read and counter electrodes to drive off the residue at a voltage about the voltage that causes hydrogen gas to form and below the voltage at which oxygen gas forms on the working electrode of the present configuration. The pulses are large enough to drive off the residue, but small enough that the carbon electrode is not electrochemically eroded. In the present system, alternating square wave pulses of −2.0 volts for 2 seconds and +2.5 volts for 4 seconds are preferred. However, voltage pulses of −1.5 to −2.5 volt and +2.0 to +3.5 volts with durations of 1–10 seconds can also produce satisfactory results.

Figure 7:
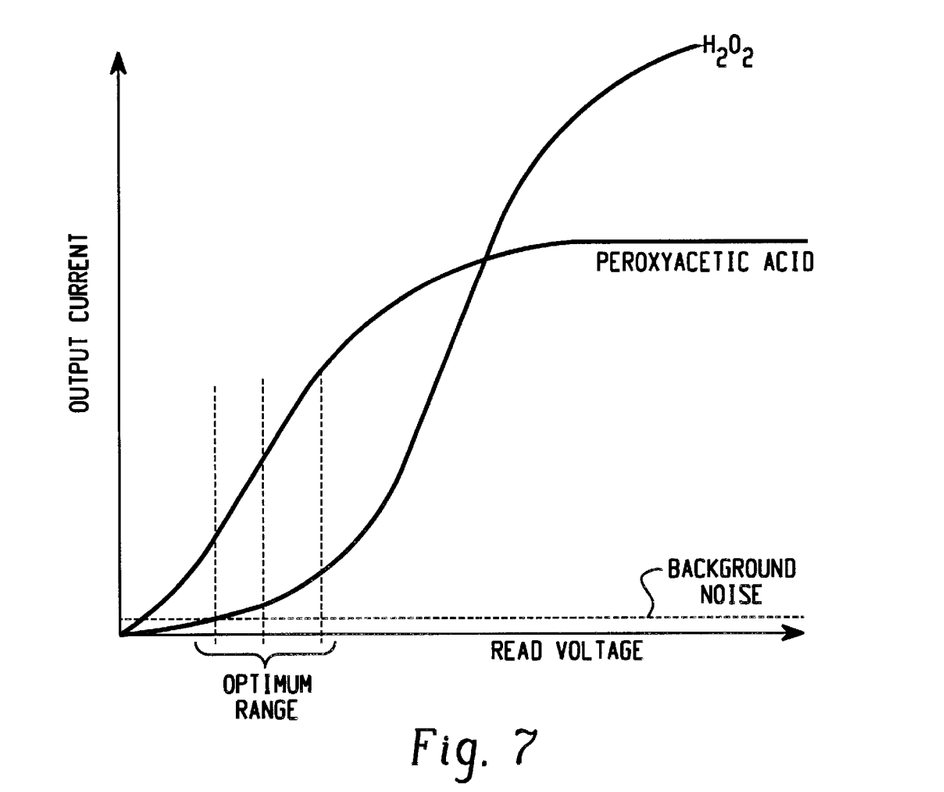
FIG. 7 is a simulated plot of current flow against read voltage for solutions containing peroxyacetic acid and hydrogen peroxide.

FIG. 7 illustrates the relationship between concentration and current flow for solutions containing fixed concentrations of hydrogen peroxide and peroxyacetic acid. At the read voltage (around −1.4 v for the system described above, relative to silver/silver chloride), the peroxyacetic acid makes a much larger contribution to the current measured than the hydrogen peroxide present. Electrode systems 110 and applied voltages are readily designed which allow the contribution of peroxyacetic acid to the current measured to be roughly ten times that of hydrogen peroxide, or greater. Unless the concentration of hydrogen peroxide in the solution to be tested is much greater than that of peroxyacetic acid, the current output in the optimal read voltage range is, for all practical purposes, dependent on the peroxyacetic acid concentration.

In some instances the optimum read voltage may not be achievable in the electrochemical system due to background noise. At low voltages (about −20 mV), the current output tends to be masked by background noise and therefore measurement of very low peroxyacetic acid concentrations, in particular, may be difficult. Thus, the choice of a preferred read voltage is dependent on the likely concentrations of peroxyacetic acid to be measured, the ratio of peroxyacetic acid to hydrogen peroxide, and the degree of background noise in the system. Using a carbon electrode pushes the optimum read voltage away from the background noise region (−20 mV). Read voltage pulses at about −1.4 volts relative to silver/silver chloride are ideal for detecting peroxyacetic acid concentrations in the range of 100 ppm to 3000 ppm, when the hydrogen peroxide concentration is less than, or not substantially greater than, the peroxyacetic acid concentration.

The choice of materials for the electrodes thus affects the selection of a preferred read voltage. Other factors, such as temperature and pH, also influence the selection.

The current output increases with temperature. Preferably, the heated housing brings the temperature of the sample to a constant temperature for measurements to be made.

Alternatively, where significant variations in temperature are anticipated, the detected current flows are preferably corrected for variations in the temperature. The thermistor 132, in this embodiment, is placed in contact with the sample to be tested and measures the temperature of the peroxyacetic acid sample. Current measurements are then compensated for variations in temperature. The computer control system 80 optionally corrects the detected current flows for variations in temperature detected by the thermistor 132. The computer preferably accesses a look-up table 196 and determines the peroxyacetic acid concentration corresponding to the current output measured. However, for automated processing systems where temperatures are controlled to within ±2–3° C., the effect of temperature on the current is relatively small and thus temperature compensation may be unnecessary.

The current generated is dependent upon the surface area of the working 118 and the counter electrode 122. Preferably, the working electrode surface area is significantly smaller than that of the counter electrode. Thus, the current flow generated for a given peroxyacetic acid concentration is limited by the working electrode surface area. The counter electrode has a larger surface area than the working electrode to avoid saturation of the electrode with electrons and a loss of the linear relationship between peroxyacetic acid concentration and current flow at higher peroxyacetic acid concentrations.

The read voltage is pulsed between the working and counter electrodes at a fixed rate. A preferred rate of pulsing is around 25 Hz (samples/sec). Because of rate limiting diffusion effects, the current output decreases asymptotically with time, eventually reaching a plateau region in which the current output is relatively constant with time. A sample time of around 5–15 seconds allows such steady state conditions to be established. The controller 112 then detects the current output, from which the peroxyacetic acid concentration is determined. Between each sampling period, the working electrode returns to the reference voltage for a period of around 5 seconds.

By repeating the sampling and the measurement of current output over a period of time, at intervals of about 30 seconds to two minutes, an accurate current measurement of the peroxyacetic acid concentration in the sterilant solution or in the sample is obtained.

When peroxyacetic acid is present in the sample, the working electrode becomes enriched with electrons when the sensing pulse is applied. This excess of electrons will tend to cause the peroxyacetic acid molecules in the vicinity of the electrode to become reduced (i.e., accept electrons from the surface of the electrode.) The movement of electrons from the electrode into the solution via this mechanism produces the electrical current that can be measured.

The magnitude of the current produced is proportional to the concentration of the peroxyacetic acid molecules close to the surface of the electrode. When the magnitude of the voltage is small, the rate at which the peroxyacetic acid molecules react is slow compared to the rate at which the peroxyacetic acid at the surface is replenished by diffusion from the bulk solution. As the voltage is increased, the rate at which peroxyacetic acid is consumed increases and, as time progresses, the concentration of peroxyacetic acid close to the electrode is depleted. This results in the current dropping exponentially and asymptotically reaching a limit determined by the rate at which peroxyacetic acid can diffuse from the bulk solution to the surface of the electrode (i.e., a diffusion limited current). The peroxyacetic acid sensor A, as it is used herein, measures this diffusion limited current. The decontaminant solution contains a buffering system which acts as an electrolyte. When a voltage is applied, a small current will flow due to the electrical conductivity of the electrolyte. In addition, when chemical species are present that are susceptible to electrochemical conversion, an additional electrical current will be produced due to electrochemical conversions at the surfaces of the electrodes.

In one embodiment, the computer control system 80 signals an alarm 202 when the peroxyacetic acid concentration of the bath drops below a preselected minimum peroxyacetic acid concentration. Or, the computer adjusts the length of the cycle to compensate for a reduced peroxyacetic acid concentration.

In another embodiment, the control system 80 adjusts the concentration of peroxyacetic acid flowing through the system in response to the detected concentration. In this embodiment, the control system signals a valve 204 in fluid communication with the fluid line 60 to open and release an additional dose of the concentrated source of peroxyacetic acid into the system from a supplementary dispenser, such as a reservoir 206, or other source of the concentrate. Other means of adjusting the peroxyacetic acid concentration are also contemplated.

Because the electrodes 118', 120', 122' in the reusable sensor A' tend to degrade over time, they should be replaced at intervals to maintain the accuracy of the sensor. Optionally, a calibration check is carried out prior to a sterilization cycle with a peroxyacetic acid containing solution or solutions of known concentration, preferably concentrations in the range to be measured. The reference electrode 120' may be checked every decontaminant cycle by measuring the magnitude of the reference potential relative to the carbon electrodes 118', 120' and/or the stainless steel housing in the presence of an electrolyte. The electrolyte may be the pretreatment mixture of buffers, corrosion inhibitors, and the like, which is circulated through the system prior to addition of the peroxyacetic acid decontaminant.

It is also important to maintain the surface condition of the working electrode, since the specific area of the working electrode affects the magnitude of the measured current. Conductivity measurement may be made periodically to provide information on the state of the electrode surface. For example, the conductivity is measured each cycle in the presence of the buffers and corrosion inhibitors. Provided that the ionic strength of the buffered solution does not vary significantly from cycle to cycle, the conductivity measurements can be used to provide an indication of the state of the working electrode surface. Theoretically, the electrical resistance between the housing and the working electrode is a function on both the surface area of the housing and the surface area of the working electrode. Since the surface area of the housing is significantly larger than that of the working electrode, the electrical resistance will be more sensitive to changes in surface area of the working electrode.

When the electrodes 118', 120', 122' are to be reused, it is preferable to maintain the working surfaces in contact with an electrolyte or water between decontaminant cycles. Accordingly, a sample of the decontaminant solution is left in the chamber at the end of a cycle. Or, the chamber is filled with a fresh solution of electrolyte or rinse water. Particularly when the system 1 is not to be used for some time, the electrodes may be removed from the sensor A' and stored in an electrolyte solution or water until needed.

In an alternative embodiment, one or more of the electrodes is disposable, while the remaining are reusable. For example, a card type sensor 125 of the type shown in FIG. 3 may be used for the working and counter electrodes 118, 122 in combination with a reusable reference electrode 120' of the type shown in FIGS. 4 and 5. The card is disposed after a decontamination cycle, and the reference electrode 120' is reused.

It will be appreciated that the peroxyacetic acid monitoring system A, A' may also be used in a variety of other peroxyacetic acid sterilization/ disinfection systems in which items to be microbially decontaminated are immersed in, or sprayed with a peroxyacetic acid solution. The system may also be used to detect the concentration of peroxyacetic acid in a bath containing peroxyacetic acid or in fluid flow lines of a water treatment system, bleaching plant, or similar system. Where the solution to be tested does not act as an electrolyte, an electrolyte may be added to the sample to be analyzed prior to making measurements.

While the system has been described with particular reference to detection of peroxyacetic acid, the system is also applicable to detection of hydrogen peroxide and other oxidizing species. By selecting an appropriate read voltage to maximize the contribution of the species to the overall output current and by choosing counter and working electrodes which are particularly suited to the species to be detected, the system may be tailored to the specific detection of a variety of species.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A decontamination process comprising:
   (a) circulating a decontaminant solution which includes peroxyacetic acid through a treatment vessel which contains items to be decontaminated;
   (b) passing a sample of the decontaminant solution from the vessel into a chamber to contact a working electrode and a counter electrode;
   (c) holding the sample in the chamber until it becomes quiescent;
   (d) after step (c), applying a voltage to the working electrode at a selected voltage relative to a reference electrode, the voltage being selected such that an output current generated between the working electrode and the counter electrode is correlated to a concentration of the peroxyacetic acid in the sample and substantially independent of a concentration of at least one other oxidizing species in the sample; and
   (e) measuring the current generated.

2. A decontamination process comprising:
   (a) circulating a decontaminant solution which includes peroxyacetic acid and hydrogen peroxide through a treatment vessel which contains items to be decontaminated;
   (b) passing a sample of the decontaminant solution containing peroxyacetic acid and hydrogen peroxide from the vessel into a chamber to contact a carbon working electrode and a counter electrode;
   (c) applying a plurality of voltage pulses to the working electrode at a selected voltage relative to a reference electrode, the voltage being selected such that an output current generated is correlated to a concentration of the peroxyacetic acid in the sample and substantially independent of a concentration of hydrogen peroxide in the sample; and
   (d) measuring the current generated.

3. The process of claim 2, further including, prior to step (c):
   applying a conditioning pulse sequence to the working electrode, the conditioning pulse sequence including a negative voltage pulse and a positive voltage pulse.

4. The process of claim 2, further including prior to step (a):
   circulating a preconditioning solution including buffers and wetting agents;
   passing a sample of the preconditioning solution into the chamber; and
   pulsing voltages between the working and counter electrodes which electrochemically remove residues from the working electrode.

5. The process of claim 2, further including, prior to step (c):
adjusting the temperature of the sample to a preselected temperature.

6. The process of claim 2, wherein step (b) includes:
flushing the chamber with the decontaminant solution.

7. The process of claim 2, wherein step (c) includes:
selecting the voltage in the diffusion limiting range.

8. The process of claim 2, wherein step (d) includes:
measuring the current generated at about ten to fifteen seconds after the start of a voltage pulse.

9. The process of claim 2, wherein step c) includes:
pulsing the voltage at a rate of about 25 pulses/second.

10. The process of claim 2, further including, after step (d):
signaling an indication of the current measured to a control system, which, in the event that the current measured is below a predetermined minimum level, conducts at least one of the following steps:
aborting the decontamination process;
extending the time of the decontamination process to compensate for the peroxyacetic acid concentration;
controlling the addition of additional peroxyacetic acid to the circulating decontaminant solution; and
providing a signal which indicates that the peroxyacetic acid concentration is below the predetermined minimum level.

11. A decontamination process comprising:
(a) circulating a decontaminant solution which includes peroxyacetic acid and hydrogen peroxide through a treatment vessel which contains items to be decontaminated;
(b) withdrawing a sample of the decontaminant solution containing peroxyacetic acid and hydrogen peroxide from the vessel and bringing it into contact with a working electrode and a counter electrode;
(c) bringing the sample to a quiescent state;
(d) pulsing a voltage of −1.2 to −1.6 volts, relative to a silver/silver chloride reference electrode, to the working electrode, the voltage being selected such that an output current generated is correlated directly to a concentration of the peroxyacetic acid in the sample and substantially independent of a concentration of hydrogen peroxide in the sample; and
(e) measuring the current generated.

12. A method of detecting a first oxidizing species in a solution which also contains a second oxidizing species, the method comprising:
disposing a carbon working electrode and a counter electrode in the solution to be tested;
pulsing a read voltage in the diffusion limiting range to the working electrode of from −1.2 to −1.6 volts so that the current flows between the working electrode and the counter electrode; and
detecting current flowing between the working electrode and the counter electrode, the read voltage being selected such that the current flowing is substantially dependent on a concentration of the first oxidizing species and substantially independent of a concentration of the second oxidizing species in the solution.

13. The method of claim 12, further including:
converting the detected current flow into an indication of the concentration of the first oxidizing species in the solution.

14. The method of claim 12, wherein the read voltage is selected such that a contribution of the first oxidizing species to the current flowing is at least ten times that of an equivalent concentration of the second oxidizing species.

15. The method of claim 12, further including:
detecting a temperature of the solution adjacent the electrodes; and
correcting the detected current flowing for a difference between the detected temperature and a preselected temperature.

16. The method of claim 12, further including:
increasing the first oxidizing species concentration in the solution when the concentration is below a preselected minimum level.

17. The method of claim 12, wherein the first oxidizing species is peroxyacetic acid and the second oxidizing species is hydrogen peroxide.

18. The method of claim 17, wherein the peroxyacetic acid concentration is in the range of 100 to 3000 ppm.

19. The method of claim 17, wherein the peroxyacetic acid concentration is determined in under one minute.

20. The method of claim 17, wherein pulsing the read voltage, and detecting current flowing are repeated at intervals of from about fifteen to thirty seconds.

21. The method of claim 12, further including:
adding an electrolyte to the sample of the solution to be tested.

22. A method of detecting a first oxidizing species in a solution which also contains a second oxidizing species, the method comprising:
disposing a working electrode formed from carbon and a counter electrode in the solution to be tested;
applying alternating 1 to 10 seconds voltage pulses of −1.5 to −2.5 volts and +2.0 to +3.5 volts between the working and counter electrodes;
pulsing a read voltage in the diffusion limiting range to the working electrode so that current flows between the working electrode and the counter electrode; and
detecting current flowing between the working electrode and the counter electrode, the read voltage being selected such that the current flowing is substantially dependent on a concentration of the first oxidizing species and substantially independent of a concentration of the second oxidizing species in the solution.

23. The method of claim 22, wherein the alternating voltage pulses are applied prior to the electrodes being disposed in the solution to be tested while the electrodes are disposed in a solution free of the oxidizing species.

24. The method of claim 23, wherein the alternating pulses are pulses +2.5 volts for 4 seconds and −2.0 volts for 2 seconds.

25. A method of detecting a concentration of peroxyacetic acid in a solution of peroxyacetic acid, water, and hydrogen peroxide independently of a concentration of the hydrogen peroxide, the method comprising:
disposing a carbon working electrode which is substantially insensitive to hydrogen peroxide at a selected voltage and a counter electrode in a quiescent sample of the solution;
pulsing a read voltage in the diffusion limiting voltage range to the working electrode creating current pulses dependent on peroxyacetic acid concentration and substantially independent of hydrogen peroxide concentration to flow between the working and counter electrodes;
detecting the current pulses between the working and counter electrodes, which detected current directly corresponds to the peroxyacetic acid concentration.

* * * * *